US00PP18314P2

(12) United States Plant Patent
Heffner

(10) Patent No.: US PP18,314 P2
(45) Date of Patent: Dec. 11, 2007

(54) *IMPATIENS* PLANT NAMED 'BODDBLVIOBI'

(50) Latin Name: *Impatiens walleriana*
Varietal Denomination: Boddblviobi

(75) Inventor: Michael Heffner, Santa Barbara, CA (US)

(73) Assignee: John Bodger + Sons Company, South EL Monte, CA (US)

( * ) Notice: Subject to any disclaimer, the term of this patent is extended or adjusted under 35 U.S.C. 154(b) by 0 days.

(21) Appl. No.: 11/483,224

(22) Filed: Jul. 7, 2006

(51) Int. Cl.
*A01H 5/00* (2006.01)

(52) U.S. Cl. ..... Plt./319

(58) Field of Classification Search ..... Plt./319
See application file for complete search history.

*Primary Examiner*—Wendy C. Haas
*Assistant Examiner*—Georgia Helmer
(74) *Attorney, Agent, or Firm*—C. A. Whealy

(57) ABSTRACT

A new and distinct cultivar of Double *Impatiens* plant named 'Boddblviobi', characterized by its compact, mounded and outwardly spreading plant habit; freely branching habit; dense and bushy growth habit; dark green-colored leaves; large double red purple and light pink to white bi-colored flowers; freely flowering habit; and flowers positioned above and beyond the foliage.

1 Drawing Sheet

Botanical designation: *Impatiens walleriana.*
Cultivar denomination: 'Boddblviobi'.

BACKGROUND OF THE INVENTION

The present invention relates to a new and distinct cultivar of Double *Impatiens* plant, botanically known as *Impatiens walleriana,* and hereinafter referred to by the name 'Boddblviobi'.

The new Double *Impatiens* is a product of a planned breeding program conducted by the Inventor in Lompoc, Calif. The objective of the breeding program was to develop new compact and freely-branching Double *Impatiens* cultivars with large double flowers, excellent branching and attractive foliage and flower coloration.

The new *Impatiens* originated from a self-pollination made by the Inventor in February, 2003, of a proprietary *Impatiens walleriana* selection identified as 2IM314-5, not patented. The cultivar Boddblviobi was discovered and selected by the Inventor as a flowering plant within the progeny of the stated self-pollination in a controlled environment in Lompoc, Calif.

Asexual reproduction of the new cultivar by terminal cuttings propagated in a controlled environment in Lompoc, Calif. since 2003 has shown that the unique features of this new Double *Impatiens* are stable and reproduced true to type in successive generations of asexual reproduction.

SUMMARY OF THE INVENTION

The cultivar Boddblviobi has not been observed under all possible environmental conditions. The phenotype may vary somewhat with variations in environment such as temperature and light intensity, without, however, any variance in genotype.

The following traits have been repeatedly observed and are determined to be the unique characteristics of 'Boddblviobi'. These characteristics in combination distinguish 'Boddblviobi' as a new and distinct cultivar of Double *Impatiens:*

1. Compact, mounded and outwardly spreading plant habit.
2. Freely branching habit; dense and bushy growth habit.
3. Dark green-colored leaves.
4. Large purple and light pink to white bi-colored flowers.
5. Double flower form.
6. Freely flowering habit.
7. Flowers positioned above and beyond the foliage.

Plants of the new *Impatiens* differ from plants of the parent selection in flower form and coloration as flowers of plants of the parent selection are single in form and have solid purple-colored flowers.

Plants of the new Double *Impatiens* can be compared to plants of the Double *Impatiens* cultivar Boddblros, disclosed in U.S. Plant Pat. No. 12,429. In side-by-side comparisons conducted in Lompoc, Calif., plants of the new Double *Impatiens* differed from plants of the cultivar Boddblviobi in the following characteristics:

1. Plants of the new Double *Impatiens* were more mounded and not as upright as plants of the cultivar Boddblros.
2. Plants of the new Double *Impatiens* were more freely branching than plants of the cultivar Boddblros.
3. Plants of the new Double *Impatiens* and the cultivar Boddblros differed in flower color as plants of the cultivar Boddblros had purple-colored flowers.

BRIEF DESCRIPTION OF THE PHOTOGRAPHS

The accompanying photographs illustrate the overall appearance of the new Double *Impatiens.* These photographs show the colors as true as it is reasonably possible to obtain in colored reproductions of this type. Colors in the photographs may differ slightly from the color values cited in the detailed botanical description which accurately describe the colors of the new Double *Impatiens.*

The photograph at the bottom of sheet comprises a side perspective view of a typical flowering plant of 'Boddblviobi' grown in a container.

The photograph at the top of the sheet comprises a close-up view of typical flowers of 'Boddblviobi'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lompoc, Calif. during the winter and spring in a polycarbonate-covered greenhouse and under conditions and practices which approximate those generally used in commercial Double *Impatiens* production. During the production of the plants, day temperatures ranged from about 21° C. to 24° C., night temperatures ranged from about 16° C. to 18° C. and light levels ranged from about 4,000 foot-candles to 8,000 foot-candles. Measurements and numerical values represent averages for typical flowering plants. Single plants were grown in 15-cm pots and were about 14 weeks old when the photographs and the detailed description were taken.

Botanical classification: *Impatiens walleriana* cultivar Boddblviobi.

Parentage: Self-pollination of a proprietary selection of *Impatiens walleriana* identified as code number 2IM314-5, not patented.

Propagation:

*Type.*—Terminal cuttings.

*Time to initiate roots.*—About two weeks at 21° C.

*Time to produce a rooted young plant.*—About four weeks at 21° C.

*Root description.*—Fine, fibrous; white in color.

*Rooting habit.*—Freely branching.

Plant description:

*Plant form.*—Compact, outwardly spreading and mounded plant habit.

*Growth and branching habit.*—Moderately vigorous and freely-branching growth habit with about 16 basal branches; secondary and eventually tertiary branches forming potentially at every node; dense and bushy growth habit. Pinching, that is removal of the terminal apex, is typically not required, but will enhance branching.

*Plant height.*—About 23 cm.

*Plant diameter or spread.*—About 47 cm.

*Lateral branches.*—Length: About 21 cm. Diameter: About 8 mm. Internode length: About 3.5 cm. Texture: Smooth, glabrous. Color: 147B tinted with 183B.

*Foliage description.*—Arrangement: Alternate, simple. Length: About 6.8 cm. Width: About 4.2 cm. Shape: Elliptical to somewhat spatulate. Apex: Broadly acute. Base: Attenuate. Margin: Crenate with sparse ciliation. Texture, upper and lower surfaces: Smooth, glabrous. Venation pattern: Pinnate. Color: Developing foliage, upper surface: Darker than 147A. Developing foliage, lower surface: 147B. Fully expanded foliage, upper surface: 147A; venation, 147B. Fully expanded foliage, lower surface: 147B tinted with 183C; venation, 147B. Petiole: Length: About 2.5 cm. Diameter: About 3 mm. Texture, upper and lower surfaces: Smooth, glabrous. Color, upper and lower surfaces: 148C.

*Flower description.*—Flower type and habit: Numerous and consistently large double flowers. Flower buds open similar to a rose in fullness; flowers rounded. Typically three flowers arranged in axillary clusters. Freely flowering, usually about 15 flowers and flower buds per lateral branch. Flowers positioned above the foliage and typically face mostly outward. Flowers last about five to seven days under greenhouse conditions. Flowers not persistent. Flowers not fragrant. Natural flowering season: Year-round under greenhouse conditions, In the garden, flowering is continuous through the spring and summer. Flower size: Diameter: About 4 cm. Depth (not including spur): About 1.5 cm. Flower buds: Length: About 1.6 cm. Diameter: About 1 cm. Shape: Ovoid. Color: 61A and 75D. Petals/petaloids: Quantity/arrangement: About 20 per flower; imbricate. Length, outer petals: About 2.2 cm. Width, outer petals: About 1.8 cm. Shape: Cordate. Apex: Emarginate. Base: Acute. Margin: Entire. Texture, upper and lower surfaces: Smooth, glabrous; velvety. Color: When opening, upper surface: Centers, 69A to 69B; towards the margins, 71A. When opening, lower surface: Centers, 75B to 75C; towards the margins, 61A. Fully opened, upper surface: Centers, 75B to 75C; towards the margins, 61A. Fully opened, lower surface: Centers, 75B to 155D; towards the margins, 71B. Sepals: Quantity/arrangement: Five in a single whorl; one modified into an elongated spur. Length: About 1.5 cm. Width: About 1.8 cm. Shape: Elliptic. Apex: Acuminate. Margin: Entire. Texture, upper and lower surfaces: Smooth, glabrous. Color, upper surface: 145D; midrib, 145A. Color, lower surface: 75C. Spur length: About 3.1 cm. Spur diameter: At flower, about 2 mm; at apex, less than 1 mm. Spur color: 145A. Peduncles: Length: About 2.6 cm. Diameter: About 2 mm. Angle: About 45° from vertical. Strength: Strong. Texture: Smooth, glabrous. Color: 148D.

*Reproductive organs.*—Flowers fully double, all stamens and pistils transformed into petaloids.

*Seed/fruit.*—Seed and fruit production have not been observed.

Disease/pest resistance: Plants of the new *Impatiens* have not been observed to be resistant to pathogens and pests common to *Impatiens*.

It is claimed:

1. A new and distinct Double *Impatiens* plant named 'Boddblviobi' as illustrated and described.

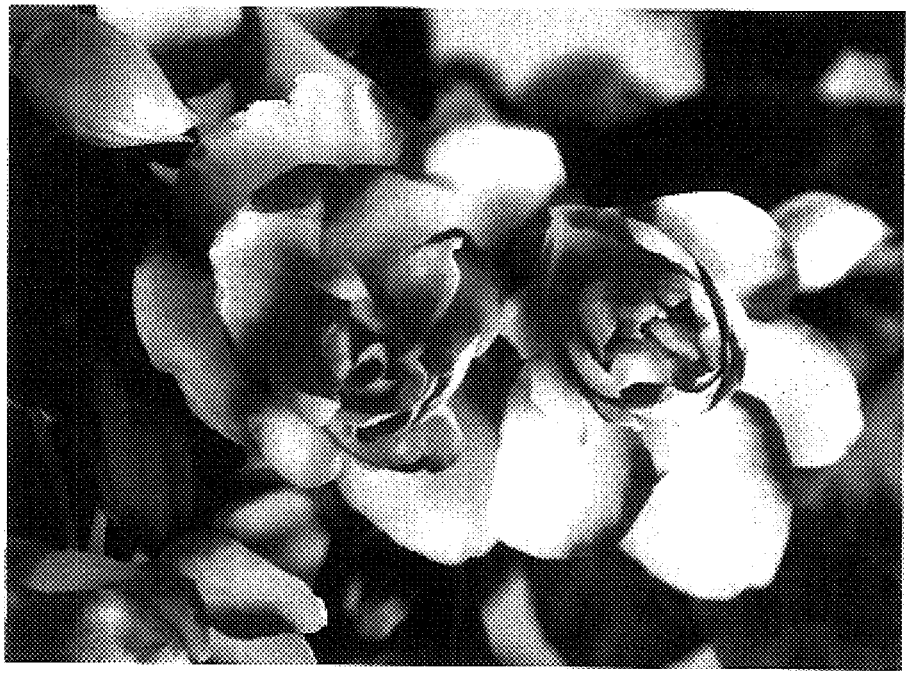
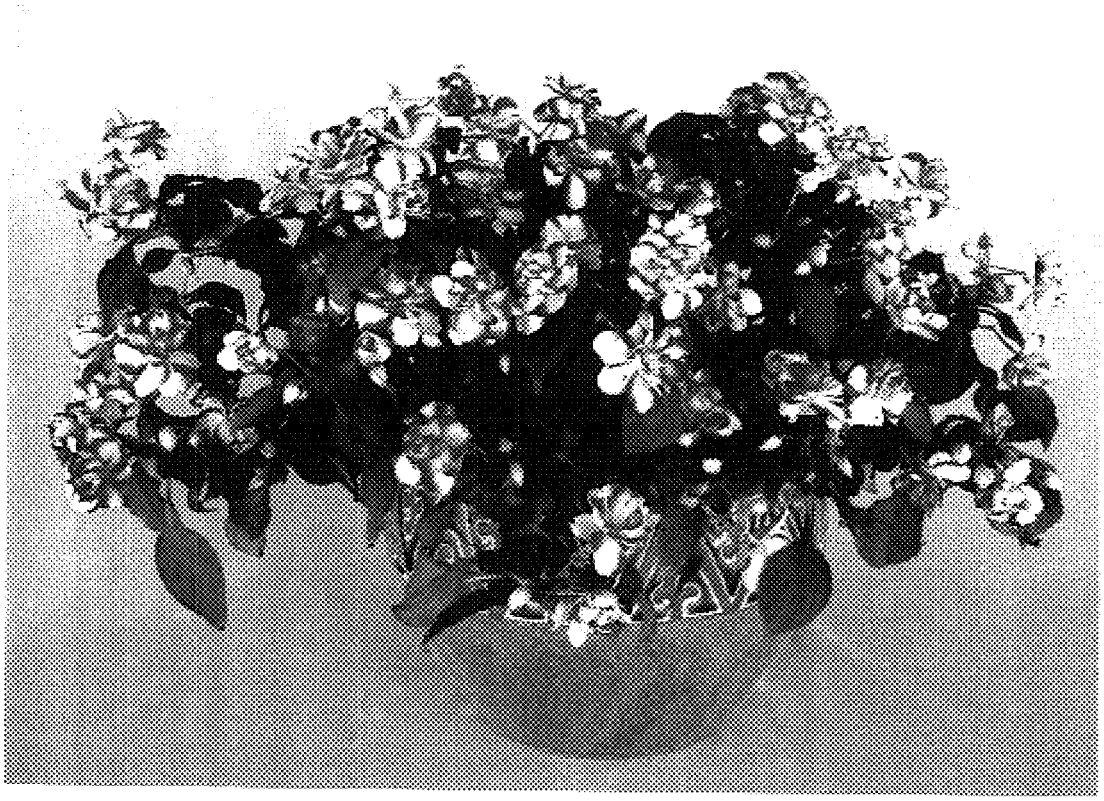

* * * * *